United States Patent
Axelrod

[11] Patent Number: 6,067,941
[45] Date of Patent: May 30, 2000

[54] ANIMAL CHEW

[75] Inventor: Glen S. Axelrod, Neptune City, N.J.

[73] Assignee: TFH Publications, Inc., Neptune City, N.J.

[21] Appl. No.: 09/303,515

[22] Filed: May 3, 1999

[51] Int. Cl.⁷ .................................................. A01K 29/00
[52] U.S. Cl. ......................... 119/707; 119/709; 119/710; 119/711
[58] Field of Search .......................... 119/707, 709–711; 601/2; 600/439; 15/167.1

[56] References Cited

U.S. PATENT DOCUMENTS

| | | | |
|---|---|---|---|
| 3,871,334 | 3/1975 | Axelrod | 119/710 |
| 4,513,014 | 4/1985 | Edwards | 426/132 |
| 4,547,376 | 10/1985 | Silver et al. | 426/102 |
| 4,557,219 | 12/1985 | Edwards | 119/29.5 |
| 4,691,718 | 9/1987 | Sakuma et al. | 433/32 |
| 4,767,630 | 8/1988 | Silver et al. | 426/102 |
| 4,771,733 | 9/1988 | Axelrod | 119/29.5 |
| 4,771,773 | 9/1988 | Kropf | 128/303 R |
| 4,985,964 | 1/1991 | Lawson | 452/135 |
| 5,007,879 | 4/1991 | Lawson | 452/198 |
| 5,138,733 | 8/1992 | Bock | 15/22.1 |
| 5,149,550 | 9/1992 | Mohilef | 426/3 |
| 5,191,856 | 3/1993 | Gordon | 119/711 |
| 5,200,212 | 4/1993 | Axelrod | 426/2 |
| 5,240,720 | 8/1993 | Axelrod | 426/2 |
| 5,247,716 | 9/1993 | Bock | 15/167.1 |
| 5,329,881 | 7/1994 | O'Rourke | 119/710 |
| 5,339,771 | 8/1994 | Axelrod | 119/711 |
| 5,369,831 | 12/1994 | Bock | 15/167.1 |
| 5,407,661 | 4/1995 | Simone et al. | 424/49 |
| 5,476,069 | 12/1995 | Axelrod | 119/709 |
| 5,635,237 | 6/1997 | Greenberg et al. | 426/646 |
| 5,711,254 | 1/1998 | O'Rourke | 119/710 |
| 5,750,196 | 5/1998 | Welch | 427/290 |
| 5,786,382 | 6/1998 | Childers-Zadah | 514/629 |
| 5,827,565 | 10/1998 | Axelrod | 426/623 |
| 5,857,431 | 1/1999 | Peterson | 119/710 |

FOREIGN PATENT DOCUMENTS

| | | | |
|---|---|---|---|
| 2254185 | 8/1975 | France | 119/709 |
| 1445019 | 8/1976 | United Kingdom | 119/709 |

Primary Examiner—Michael J. Carone
Assistant Examiner—Daniel Beitey
Attorney, Agent, or Firm—Hayes, Soloway, Hennessey, Grossman & Hage, P.C.

[57] ABSTRACT

An improved animal chew comprising a low voltage battery and various conductors such that when an animal chews on the present invention an electrical circuit is formed and a micro-current flows. This micro-current has therapeutic effects on the animal's teeth and gums, and optionally, low concentrations of certain trace metals are released which similarly have beneficial results regarding the animal's oral hygiene. In addition, upon chewing, calcium ions and/or fluoride ions can be discharged. Finally, in optional embodiment, ultrasonic sound waves can be generated when an animal chews on the present invention which further assists in removal of plaque from the animal's teeth and gums.

19 Claims, 3 Drawing Sheets

ANIMAL CHEW

FIELD OF THE INVENTION

The present invention relates to an improved animal chew toy comprising a battery and conductors such that when an animal chews on the invention a micro-current is caused to flow.

BACKGROUND OF THE INVENTION

U.S. Pat. No. 5,827,565 provides that most dogs enjoy chewing on various objects, although preferences vary as to the desired hardness of those objects. Some dogs like to chew on very hard materials such as cow bones, wood, nylon, and the like. Some dogs, due to their age, may not be able to chew on very hard substances. Young dogs may have insufficiently developed teeth, while older dogs may have diseased gums or may have lost some of their teeth.

The prior art is replete with examples of hard chews, soft chews, indigestible chews, and digestible chews. All of these prior art animal chews, however, rely exclusive on mechanical action, i.e. the animal's chewing action, to assist in removal of plaque from the animal's teeth.

For example, Applicant's assignee, T.F.H. Publications, Inc. has previously developed an edible dog chew that is wholly digestible, nutritious and maintains a texture or hardness which is individually adjustable by application of heat to suit a wide variety of preferences or needs. Such dog chews utilize a mixture of primarily casein and are described in U.S. Pat. Nos. 5,200,212 and 5,240,720.

In Applicant's U.S. Pat. No. 5,827,565 there is disclosed a process for making a heat expandable dog chew comprised primarily of injection molded potato starch granules and an attractant. Attractants recited include chicken powder, liver powder, ham, turkey, beef and/or fish. Natural vegetable additives such as spinach or carrots may also be added.

In Applicant's U.S. patent application Ser. No. 09/138,804, which as noted is a continuation-in-part of U.S. Pat. No. 5,827,565, there is disclosed a dog chew having natural fruit flavor to increase the dog's appetite for such chew. The preferred form of such edible chew maintained the basic ingredient of a heat-expandable starch, such as potato starch.

Attention is also directed to the following U.S. patents and copending applications, commonly owned by the assignee herein: U.S. Pat. No. 5,476,069; U.S. patent application Ser. No. 08/923,070 filed Sep. 3, 1997 entitled "Vegetable Based Dog Chew"; Ser. No. 08/738,423 filed Oct. 25, 1997 entitled "Edible Dog Chew"; Ser. No. 08/784,834 filed Jan. 17, 1997 entitled "Carrot-Based Dog Chew"; Ser. No. 08/888,611 filed Jul. 7, 1997 entitled "Vegetable Dog Chew"; Ser. No. 09/114,872 filed Jul. 14, 1998 entitled "Heat Modifiable Edible Dog Chew"; Ser. No. 09/138,804 filed Aug. 21, 1998 entitled "Improved Edible Dog Chew"; Ser. No. 09/116,070 filed Jul. 15, 1998 entitled "Wheat & Casein Dow Chew With Modifiable Texture"; Ser. No. 09/116,555 filed Jul. 15, 1998 entitled "Heat Modifiable Peanut Dog Chew"; Ser. No. 09/227,767 filed Jan. 8, 1999 entitled "Method of Molding Edible Starch." In addition to such patents and applications, attention is also directed to the art cited in said patents and applications, as such art relates to the field of molded starch products.

In addition, the prior art has recently grown to include a variety of other disclosures directed at flavored pet products. For example, U.S. Pat. No. 5,786,382 entitled "Use of Valerian Plant and/or Root as a Scent-Attractant for Stimulating Canine and Felines." This patent discloses the use of the herb/plant Valerian in all of its forms, whether whole or in part, for use in a food product, whereby the natural aroma emitted by the Valerian plant will attract dogs and cats.

U.S. Pat. Nos. 4,985,964 and 5,007,879 entitled "Dog Chew Processing Method" disclose methods for processing cattle hoofs for use as a dog chew product. U.S. Pat. No. 5,149,550 entitled "Methods for Making Pet Chews" discloses that ligaments from cattle and other hoofstocks are rendered substantially free of fat and can be dried and hardened for use as a pet chew.

U.S. Pat. No. 5,407,661 entitled "Pet Chew Product Having Oral Care Properties" discloses an edible pet chew product having a flexible cellular matrix in which is contained cellulosic fibrous material such as corn cob fractions which are described as having a mechanical cleansing function when chewed by a pet.

U.S. Pat. No. 5,635,237 entitled "Method of Manufacturing Substantially Pure Rawhide Pet Products" discloses a chew of pure rawhide utilizing twin screw extrusion with multiple heating zones and interchangeable extrusion dies.

U.S. Pat. No. 5,711,254 entitled "Dog Chew Toy" discloses a chew toy for dogs formed of a length of composite rope having an inner core defined by strands of twisted threads of natural plant or synthetic fibers and a soft outer shell defined by a plurality of strands of soft cotton threads twisted about the inner core. The inner core is said to be less water absorbent than the outer shell to promote drying of the toy when wetted with dog saliva to inhibit bacteria growth.

U.S. Pat. No. 5,750,196 entitled "Process for Manufacturing Dog Chew Toys of Tire Sidewalls" discloses the use of a dye to cut toy bases from sidewalls recovered from used tires.

Other earlier examples of such products are disclosed in U.S. Pat. No. 3,871,334 to Axelrod (nylon substrate containing liquid flavor and odor components), U.S. Pat. No. 4,771,733 to Axelrod (polyurethane toy containing aqueous-based flavor and odor components), and U.S. Pat. Nos. 4,557,219 and 4,513,014 to Edwards (use of flavorings in a molded polyurethane dog chew).

In U.S. Pat. No. 4,691,718, Sakuma et al. disclose a toothbrush molded from an ion eluting-type ceramic and containing a battery. During use a circuit is formed via the user's hand, arm, and body thereby releasing calcium or fluoride ions.

In U.S. Pat. No. 4,969,868, Wang discloses a tooth brush containing a battery and wherein certain special bristles act as a cathode. A metal plate adjacent to the brush head serves as an anode. Use of ionized toothpaste completes the circuit such that current flows.

In U.S. Pat. No. 5,138,733, Bock discloses a toothbrush which generates ultrasonic sound waves. These ultrasonic sound waves assist in plaque removal from the user's teeth.

The animal chew products disclosed previously utilize mechanical energy alone, i.e. the animal's chewing action, to remove plaque from the animals' teeth and to strengthen the animals gums. Accordingly, it is an object herein to improve further upon these prior art pet chew products. Specifically, it is also an object herein to utilize the flow of electricity across a pet chew product to strengthen an animals' teeth and gums. It is a further object herein to utilize the release of certain trace elements and/or ions from a pet chew product to strengthen an animal's teeth. Furthermore, it is an object herein to utilize ultrasonic sound waves generated within a pet chew product to assist cleansing an animal's teeth and gums.

SUMMARY OF THE INVENTION

An improved animal chew comprising a low voltage battery and various conductors such that in the dry, unused state, no current flows. However, when an animal chews on the present invention an electrical circuit is formed and a micro-current flows. This micro-current has therapeutic effects on the animal's teeth and gums. In alternative embodiment, low concentrations of certain trace metals are released when an animal chews on the present invention. Release of these trace metals has beneficial results regarding the animal's oral hygiene.

In yet another alternative embodiment, calcium ions and/or fluoride ions are released from an ion eluting-type ceramic when an animal chews on the invention. Finally, in yet another alternative embodiment, ultrasonic sound waves are generated when an animal chews on the present invention. These sound waves assist in removal of plaque from the animal's teeth and gums.

BRIEF DESCRIPTION OF THE DRAWINGS

The invention will be better understood from a reading of the following detailed description taken in conjunction with the drawings in which like reference designators are used to designate like elements, and in which:

FIG. 1A is a front view of a battery charger;

DETAILED DESCRIPTION OF THE PREFERRED EMBODIMENTS

Figure 1:
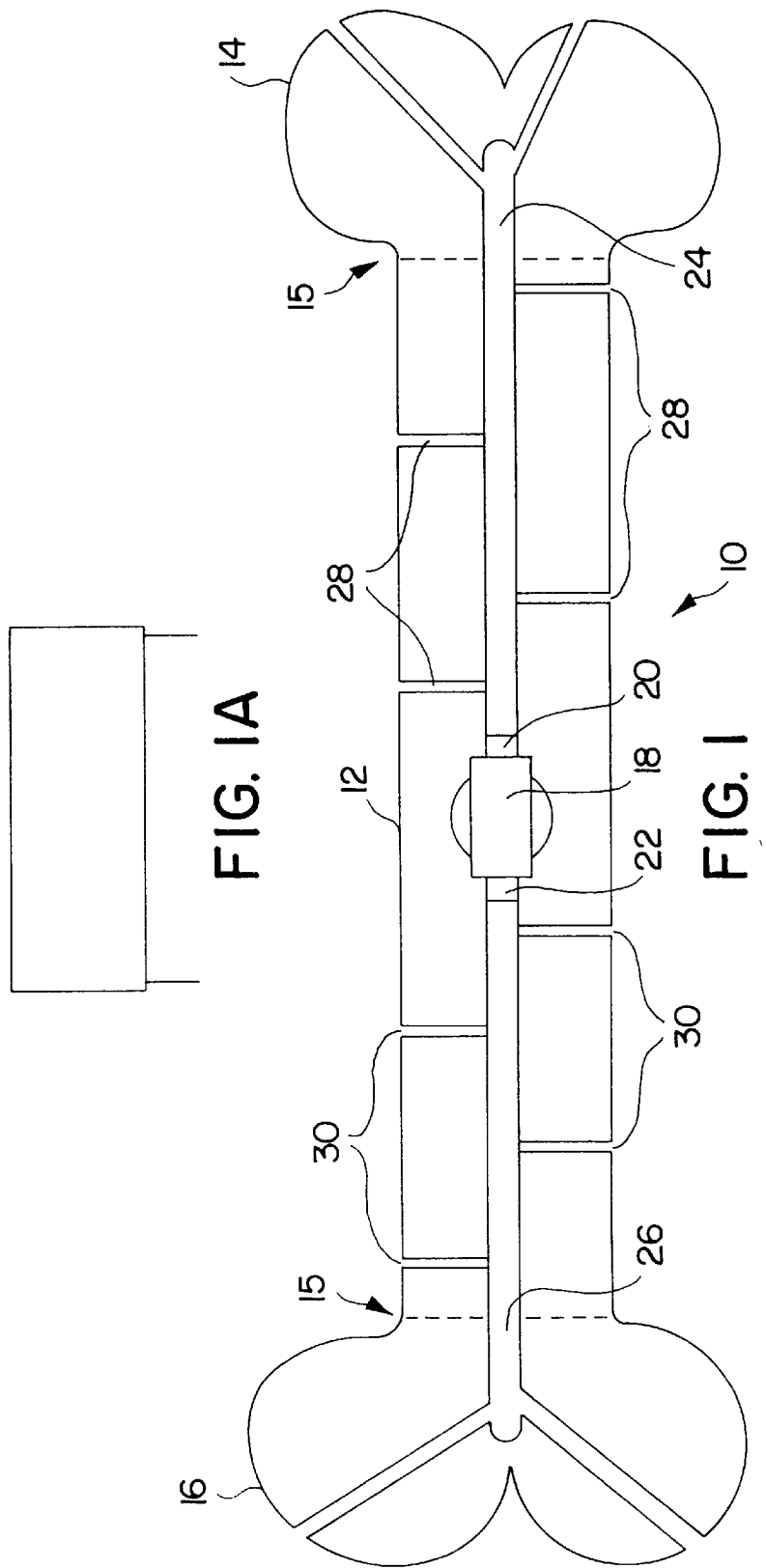
FIG. 1 is a longitudinal cut-away view illustrating an embodiment of an animal chew according to the present invention.

With reference first to FIG. 1, there is shown an animal chew embodying the present invention. The animal chew 10 internally accommodates a miniature battery 18 the battery being optionally rechargeable. The voltage of the battery can be about 1.5 v to about 4.5 v. Battery 18 comprises first pole 20 and second pole 22.

First conductor 24 is coupled to first pole 20 and extends in one direction though the interior of the animal chew 10. First conductor 24 exposes outward via a plurality of first holes 28.

Similarly, second conductor 26 is coupled to second pole 22 on battery 18 and extends through the interior of animal chew 10 in the direction opposite to that of said first conductor. Second conductor 26 exposes outward via a plurality of second holes 30.

As will be appreciated by those skilled in the art, first conductor 24 and second conductor 26 can be formed using conventional materials such as copper or aluminum. Furthermore, first conductor 24 and second conductor 26 can be a solid member or can be formed from stranded wiring. In the alternative, first conductor 24 and/or second conductor 26 can be formed from electrically conductive polymeric materials, such as filled epoxy and/or polyurethane resins. Alternatively, electrically conductive polymeric materials such as polyacetylene can also be used to form first conductor 24 or second conductor 26.

The present invention can be formed into a variety of forms. As shown in FIG. 1, the present invention can be molded into the form of a bone. In the alternative, the present invention can also be formed into the shape of a ring, a disk, or a rod.

Referring to FIG. 1, middle portion 12, first end portion 14, and second end portion 16, of animal chew 10 may be molded separately, and the first conductor and the second conductor may then be inserted into the first end portion and the second end portion, respectively, to form a unitary body. Alternatively, the middle portion and the end portions may be integrally molded beforehand to form the unitary body. The middle portion and the end portions may be molded from any number of synthetic resins including nylon, polyurethane, polyethylene, polypropylene, polystyrene and mixtures thereof.

The middle portion 12 and the first end portion 14 are provided with a plurality of first holes 28. Alternatively, first holes may be directed only to the end portion. First holes 28 expose the first conductor to the surface of animal chew 10. First holes 28 may have the form of slender slots.

In addition, first holes 28 can be readily made towards the surface of the end portion 14, where the animal typically invokes its chewing action. Accordingly, by placing holes to the end portion 14, the end portion can also be conveniently configured to be a replaceable component 15 of the chew 10 when worn by chewing. In addition, in such preferred configuration, battery 18 can be placed in a more secure and permanent/rigid housing in the chew 10, thereby providing a chew 10 with a strong rigid central portion, yet replaceable flexible portions 14 and 16 which flexible portions 14 and 16 can be selectively made to attract the animal's chewing action. That is, the flexibility alone will attract chewing away from the central portion of the chew 10, and as discussed herein, flavorings and attractants can also be added to the portions 14 and 16 as an even further incentive to isolate animal chewing action thereon.

The middle portion 12 and the second end portion 16 are provided with a plurality of second holes 30. Second holes 30 expose the second conductor to the surface of animal chew 10. Second holes 30 may have the form of slender slots. Similar to first holes 28, second holes 30 are preferably configured to reach end portion 16, where again, the animal commonly chews. In addition, like end portion 14, end portion can be made replaceable 15, and/or flexible, and/or flavored, so that when worn by chewing it can be replaced.

The animal's saliva functions as an automatic on-off switch. When the animal chew is not used and is dry, it is in the state of an open circuit. However when an animal chews on the invention, the animal's saliva spreads across the chew product filling one of more of first holes 28 and also filling one or more of second holes 30, thereby forming a complete circuit to the battery. As will be appreciated by those skilled in the art, the dimensions of first holes 28 and second holes 30, i.e. the depth and diameter, are adjusted to facilitate capillary action which "wicks" the animal saliva into the holes thereby filling those holes.

The micro-current flowing through the closed circuit stimulates the soft tissues in the animal's oral cavity and gums as the animal chews the object so as to encourage blood circulation, regulate the nerve endings and improve the soft tissues in the animal's oral cavity. Thus, the flow of current across the animal's teeth and gums works in conjunction with the mechanical action of chewing to facilitate oral hygiene and plaque removal.

In accordance with the present invention, attractants may be added during the molding process. Natural attractants are preferred. As will be appreciated by those skilled in the art, such attractants may comprise both powders and liquids, and are derived from meat, fish and poultry derivatives, as well as from dairy products, such as cheese formulations. For example, attractants such as chicken powder, liver powder, ham, turkey, beef and/or fish in the amount of 1–5% by weight may be used.

In addition, a food coloring may be added prior to molding to enhance the attractiveness of the chew to a particular animal. The weight content of such food coloring in the present invention may be between about 0.05% and about 10.0% (wt).

In another embodiment of the present invention, the animal chew of the present invention may be formed from an ion eluting-type ceramic material. Again referring to FIG. 1, middle portion 12 may be formed from such an ion eluting-type ceramic material. Such a ceramic middle portion can then be joined with the end portions 14 and 16 which may also be formed from such an ion eluting-type ceramic, or which may be formed from a thermoplastic resin. In the alternative, the entire animal chew 10 may be integrally formed from an ion eluting-type ceramic.

As the animal saliva closes the electrical circuit such that current flows, calcium ions, fluoride ions, or complexes thereof, elute from the ceramic component. These released ions are deposited onto and penetrate the animal's tooth surfaces and dental pulpa. The animal's teeth and dental pulpa are thus strengthened and improved in appearance by the calcium or fluoride ion while plaque is removed from the surface of the animal's teeth by electronic decomposition. The preferred ion eluting-type ceramic is a apatite ceramic such as hydroxy apatite, $Ca_{10}(PO_4)_6(OH)_2$, or apatite fluoride, $Ca_{10}(PO_4)_6F_2$.

The molded apatite ceramic may be obtained by adding about 10 wt-% to about 30 wt-% of a silicone acryl polymer or acryl resin to about 70 wt-% to about 90 wt-% of hydroxy apatite or apatite fluoride mixing the two together, applying a pressure of about 500–700 kg/cm$^2$ at room temperature and molding the mixture as in the manner of an ordinary plastic.

In an additional embodiment of the invention, the first conductor and/or the second conductor may include certain trace elements. When the animal's saliva closes the electric circuit and current flows, low concentrations of these trace elements are released. The presence of such low concentrations of these trace element ions will help to prevent tooth decay, and will additionally encourage cementosis. The trace elements of use in this embodiment include molybdenum, cobalt, vanadium, beryllium, platinum, rhenium, and mixtures thereof.

Figure 2:
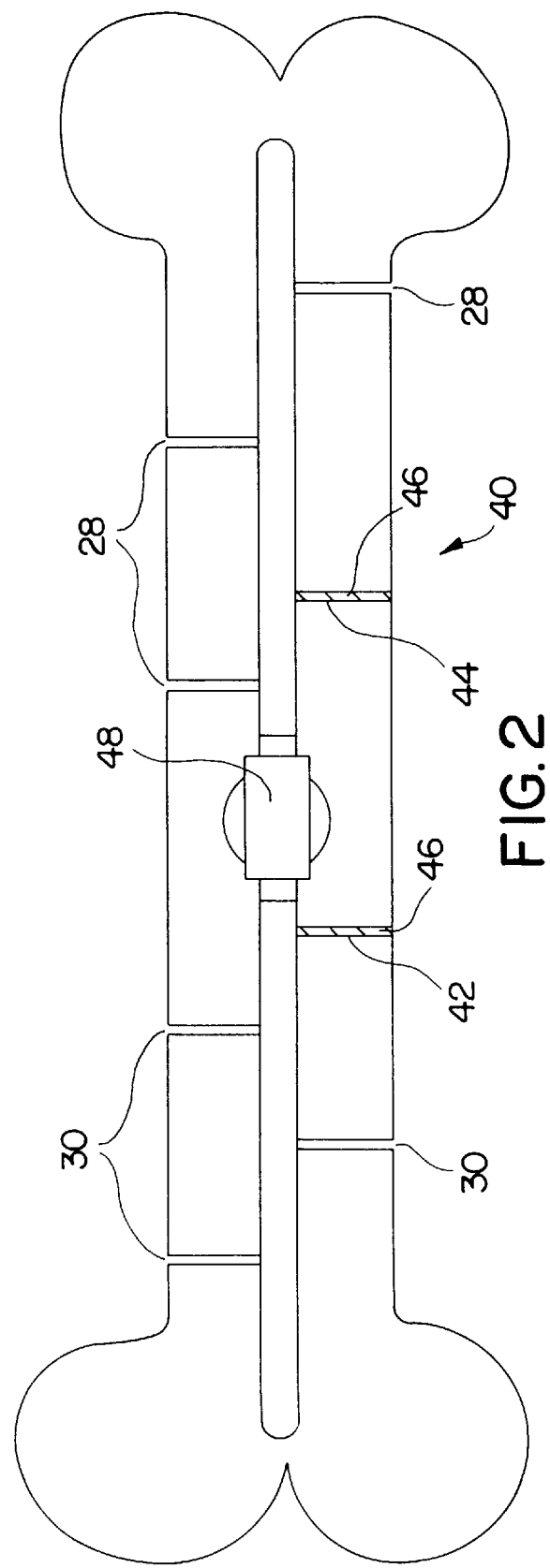
FIG. 2 is a longitudinal cut-away view illustrating an alternative embodiment of the present invention which includes a rechargeable battery and a means to recharge same.

In an alternative embodiment, one or more of first holes 28, and one or more of second holes 30, can be filled with an electrically conductive material. For example as shown in FIG. 2, hole 42 is filled with electrically conductive material 46, and hole 44 is also filled with electrically conductive material 46. As will be appreciated by those skilled in the art, there exists a wide variety of electrically conductive binders and adhesives available that may be used as electrically conductive material 46. Such materials generally comprise a base resin, such as an epoxy or a polyurethane, which contain dispersed therein sufficient metal particles to render the filled resin electrically conductive.

In this embodiment, the animal saliva need only bring the surface of one or more of such filled first holes into electrical contact with the surface of one or more of such filled second holes to complete the circuit. In addition, in this embodiment battery 48 comprises a rechargeable battery. A battery charger, illustrated in FIG. 1A, can be connected to rechargeable battery 48 via filled hole 42 and filled hole 44 to allow recharging of the battery.

Figure 3:
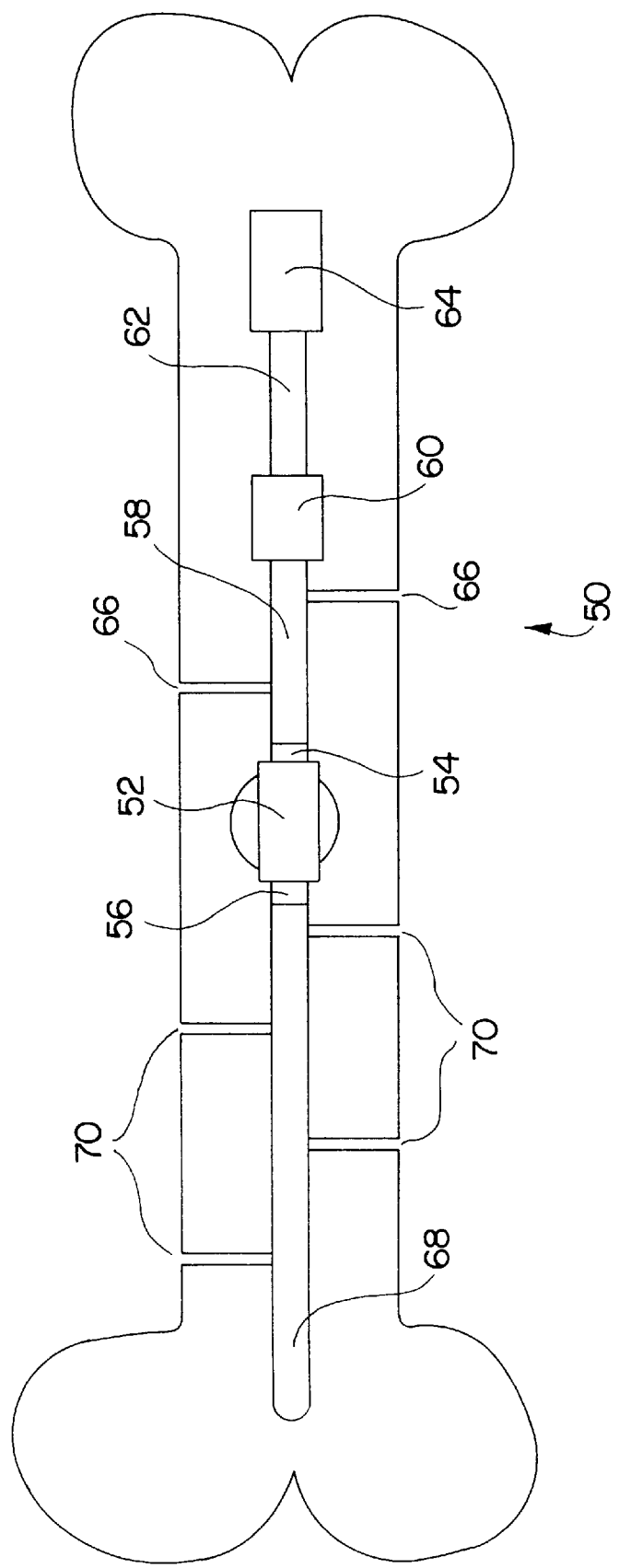
FIG. 3 is a longitudinal cut-away view illustrating a third embodiment of the present invention which includes an ultrasonic sound wave generating component.

With reference to FIG. 3, there is shown an alternative embodiment of the present invention. The animal chew 50 accommodates miniature battery 52 having first pole 54 and second pole 56. The voltage of the battery can be about 1.5 v to about 4.5 v. As discussed above, said battery 50 can be of a rechargeable type.

First conductor 58 is coupled to said first pole and is also coupled to an electronics driving module 60. Electronics driving module 60 is connected to piezoelectric transducer 64 via third conductor 62. The first conductor 58 exposes to the surface of the animal chew via a plurality of first holes 66. As discussed above, one or more of the plurality of first holes 66 can be filled with an electrically conductive material.

Again referring to FIG. 3, second conductor 68 is coupled to said second pole 56 on battery 52, and extends through the interior of animal chew 50 in the direction opposite to that of first conductor 58. Second conductor 68 exposes outward via a plurality of second holes 70. As discussed above, one or more of the plurality of second holes 70 can be filled with an electrically conductive material.

Once again, the animal's saliva functions as an automatic on-off switch. When the animal chew is not used and is dry, it is in the state of an open circuit. However when an animal chews on the invention, saliva spreads across the chew object and fills one or more of first holes 66 and second holes 70, thereby forming a complete circuit to the battery. As will be appreciated by those skilled in the art, the dimensions of first holes 66 and second holes 70, i.e. the depth and diameter, are adjusted to facilitate capillary action which "wicks" the animal saliva into the holes thereby filling those holes.

As the circuit is closed, the low voltage DC energy supplied by battery 52 is converted to an ultrasonic frequency current by electronics driving module 60. The piezoelectric crystal resonates, expands and contracts volumetrically, in tune with the frequency supplied by the electronics driving unit 60 via third conductor 62, and thereby, converts the electronic energy into ultrasonic sound-wave energy.

As will be appreciated by those skilled in the art, electronics driving unit 60 may in the alternative convert the DC energy supplied by the battery 52 into sonic frequency current. This being the case, the piezoelectric transducer generates sonic sound-wave energy.

The ultrasonic/sonic sound waves generated within the animal chew then drive the animal's saliva against the animal's teeth causing mild cavitation within the saliva at the junction with the teeth, resulting in a loosening effect on the soft plaque on the surface of the teeth and in the periodontal pockets formed in the gums around the neck of the animal's teeth. The loosened plaque is then dislodged by the animal's chewing action on the animal chew.

What is claimed is:

1. An animal chew comprising:
   a battery accommodated within said animal chew, said animal chew toy containing a chewing surface, wherein said battery comprises a first pole and a second pole;
   a first conductor connected to said first pole of said battery, said first conductor extending in one direction from said first pole in said animal chew and outwardly exposed via a first hole on said animal chew to said chewing surface; and a second conductor connected to said second pole of said battery, said second conductor extending from said second pole in a second direction and outwardly exposed via a second hole on said animal chew.

2. The animal chew toy of claim 1, wherein said animal chew further contains a plurality of first and second holes for outwardly exposing said first and second conductor.

3. The animal chew toy of claim 1, wherein said first or second hole for outwardly exposing said first or second conductor is filled with electrically conductive material.

4. The animal chew toy of claim 3 wherein said electrically conductive material comprises an epoxy or polyurethane resin having metal particles dispersed therein.

5. The animal chew toy of claim 1, wherein said animal chew comprises nonconductive material and said first and second conductors are contained completely within said animal chew.

6. The animal chew toy of claim 5 wherein said nonconductive material is a plastic or elastomeric material.

7. The animal chew of claim 1, wherein said battery comprises a rechargeable battery.

8. The animal chew of claim 7, further comprising a device for charging said rechargeable battery wherein said rechargeable battery is recharged through said first and second holes.

9. The animal chew of claim 1, comprising an integrally molded body of a thermoplastic resin.

10. The animal chew of claim 9, wherein said thermoplastic resin is selected from the group consisting of nylon, polyurethane, polyethylene, polypropylene, polystyrene, and mixtures thereof.

11. The animal chew of claim 1 wherein said chew toy contains an ion eluting-type ceramic.

12. The animal chew of claim 11 wherein said ion eluting-type ceramic is selected from the group consisting of a hydroxy apatite, a apatite fluoride, and mixtures thereof.

13. The animal chew of claim 1, wherein said chew toy contains a thermoplastic resin and an ion eluting-type ceramic.

14. The animal chew of claim 1, having the shape of a bone, ring or disk.

15. The animal chew of claim 1, wherein said first or second conductor comprises a trace element which releases ions upon conduction of current.

16. The animal chew of claim 15 wherein said trace element is selected from the group consisting of molybdenum, cobalt, vanadium, beryllium, platinum, rhenium, and mixtures thereof.

17. The animal chew of claim 1, further comprising:

a piezoelectric transducer for generating vibrations of ultrasonic frequency by contracting and expanding volumetrically in response to a changing electrical field;

a third conductor; and source for generating said changing electrical field coupled to said battery by said first conductor and transmitting said changing electrical field to said piezoelectric transducer via said third conductor.

18. The animal chew toy of claim 1, wherein said animal chew toy contains end portions and said outwardly exposed first and second holes are outwardly disposed to said end portions, and said end portions are connected to said chew toy so that said end portions can be disconnected from said chew toy.

19. The animal chew toy of claim 18, wherein said end portions contain an attractant.

* * * * *